(12) United States Patent
Bader et al.

(10) Patent No.: US 9,808,380 B2
(45) Date of Patent: Nov. 7, 2017

(54) ABSORBENT ARTICLE WITH ELASTICALLY ELONGATABLE PANEL

(71) Applicant: The Procter & Gamble Company, Cincinnati, OH (US)

(72) Inventors: Herbert Bader, Norwalde (DE); Horst Kurrer, Gronau (DE); Marcel Grossmann, Essen (DE); Olga Fezert, Lingen (DE)

(73) Assignee: The Procter & Gamble Company, Cincinnati, OH (US)

( * ) Notice: Subject to any disclaimer, the term of this patent is extended or adjusted under 35 U.S.C. 154(b) by 710 days.

(21) Appl. No.: 14/284,431

(22) Filed: May 22, 2014

(65) Prior Publication Data
US 2014/0358107 A1    Dec. 4, 2014

Related U.S. Application Data

(60) Provisional application No. 61/827,774, filed on May 28, 2013.

(51) Int. Cl.
| | | |
|---|---|---|
| *A61F 13/15* | (2006.01) | |
| *A61F 13/49* | (2006.01) | |
| *A61F 13/62* | (2006.01) | |
| *A44B 18/00* | (2006.01) | |
| *A61F 13/56* | (2006.01) | |

(52) U.S. Cl.
CPC .... *A61F 13/49015* (2013.01); *A44B 18/0069* (2013.01); *A61F 13/15756* (2013.01); *A61F 13/5633* (2013.01); *A61F 13/622* (2013.01); *A61F 13/625* (2013.01); *A61F 13/627* (2013.01); *Y10T 24/2767* (2015.01)

(58) Field of Classification Search
CPC .... A61F 13/622; A61F 13/625; A61F 13/627; A61F 13/49015; A61F 13/5633; A44B 18/0069; Y10T 24/2767
USPC ................................................. 604/387, 391
See application file for complete search history.

(56) References Cited

U.S. PATENT DOCUMENTS

| | | |
|---|---|---|
| 5,846,262 A | 12/1998 | Sayama et al. |
| 7,422,991 B2 | 9/2008 | Baldauf et al. |
| 8,337,651 B2 | 12/2012 | Schoenbeck |
| 8,496,773 B2 | 7/2013 | Bader et al. |
| 2013/0230700 A1 | 9/2013 | Schoenbeck |

FOREIGN PATENT DOCUMENTS

| | | |
|---|---|---|
| EP | 768075 B1 | 2/2003 |
| EP | 1736306 A1 | 12/2006 |
| EP | 2301502 A1 | 3/2011 |
| EP | 2340796 A1 | 7/2011 |
| EP | 2564822 | 6/2013 |

OTHER PUBLICATIONS

International Search Report, PCT/US2014/038127, mailed Aug. 20, 2014, 9 pages.

*Primary Examiner* — Jacqueline Stephens
(74) *Attorney, Agent, or Firm* — Wednesday G. Shipp

(57) ABSTRACT

Closure elements that include elastic and non-elastic regions are disclosed as well as absorbent articles that include closure elements.

20 Claims, 11 Drawing Sheets

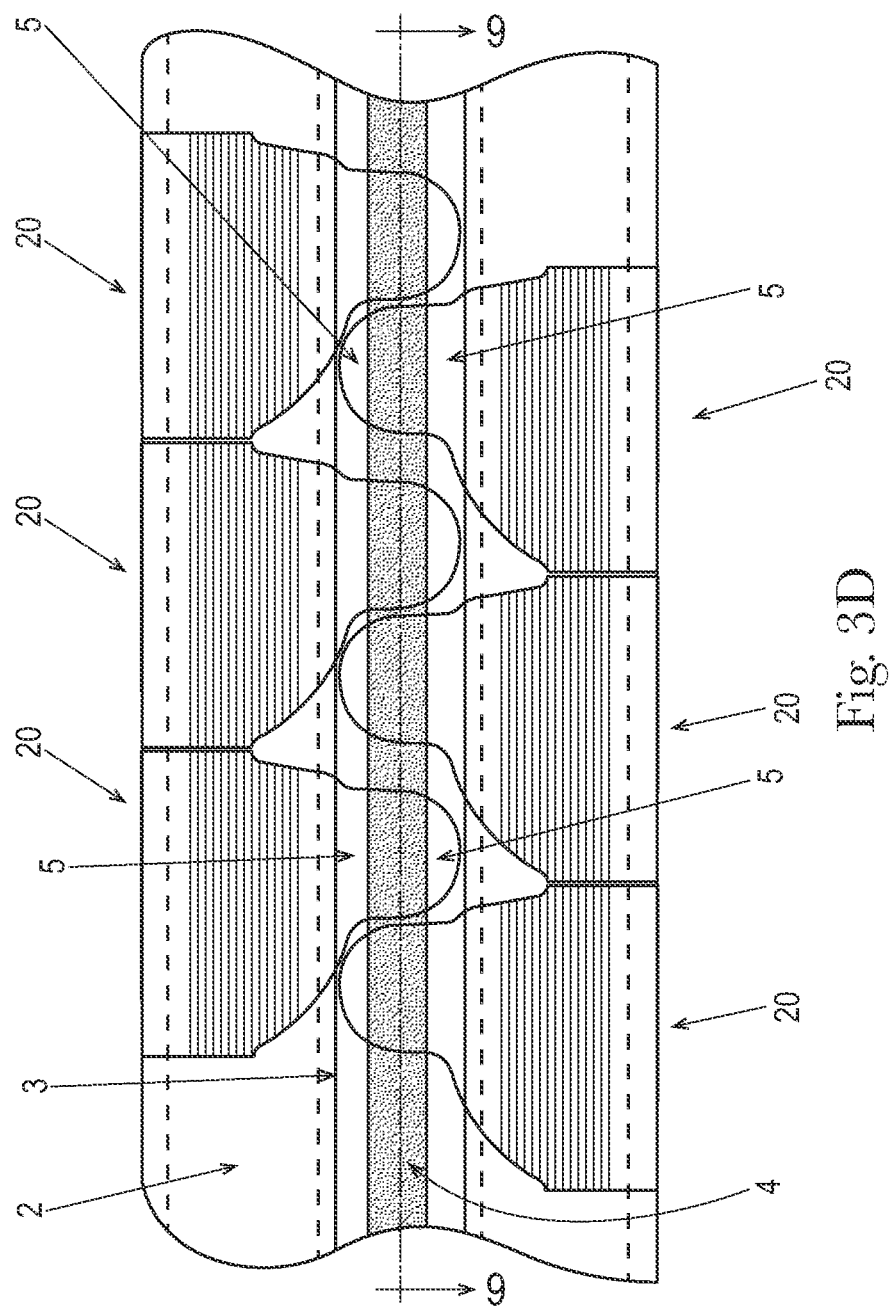

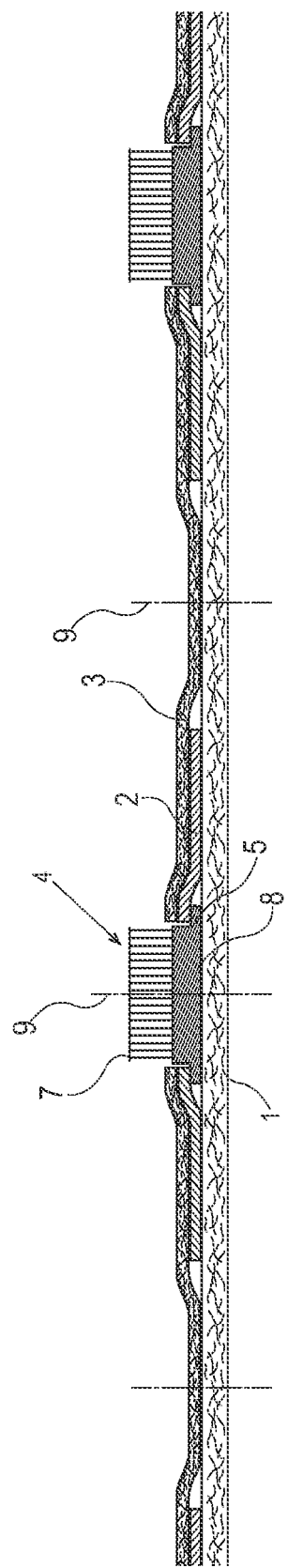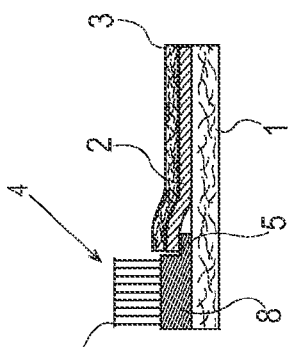

ABSORBENT ARTICLE WITH ELASTICALLY ELONGATABLE PANEL

FIELD OF THE INVENTION

The disclosure generally relates to absorbent articles comprising at least one elastically elongatable panel that includes a mechanical fastener.

BACKGROUND OF THE INVENTION

In one aspect, the invention relates to an absorbent article that includes an elastically elongatable panel. The elastically elongatable panel may be obtained by cutting a compound material web having elastic and non-elastic regions and that is adapted to be used as a closure element. The compound material web comprises a nonwoven web forming a first outer side of the compound material web, an elastomeric material disposed on the nonwoven web, a nonwoven material disposed on the elastomeric material and forming a second outer side of the compound material web and at least one non-elastic strip of a fastening material.

EP 2301502 A1 discloses the manufacture of compound material webs useful as closure elements, by laminating elastic strips in between two flat nonwoven webs. This publication discloses that a reinforcement strip is inserted between two adjacent elastically stretchable film strips. A strip of fastening material is joined to the reinforcement strip, which prevents the nonwoven material from uncontrollably tearing when the compound material web is under tension. The reinforcement strip also overlaps with the elastically stretchable film strip.

A compound material web with elastic and non-elastic areas is also disclosed in EP1736306A1. Elastic and non-elastic areas are formed in this publication by applying a continuous layer of adhesive. The continuous layer of adhesive reinforces the material to a sufficient degree whereas a discontinuous application of adhesive on the elastically stretchable film strips allows the web to elongate in its cross-direction. Bit it is believed that subsequent attachment of a fastening material on the outer side of the web can be problematic because the material below the hook strip is reinforced only by a continuous adhesive layer.

EP2340796A1 discloses a compound material web having a fastening material that is glued externally onto one of two flat nonwoven webs. In order to give the material sufficient strength an additional non-elastic strip of material is provided as reinforcement on the opposite side. It is believed however that the application of two opposing non-elastic material strips may be overly expensive from a material as well as process point of view.

EP768075B1 discloses an absorbent article with lateral closure elements which do not have any elastic areas. The necessary overall elasticity of the disposable nappy is achieved by arranging an elastic element in the waist region. The closure elements in this publication are in the form of lateral wings that are "rigid" and presumably are not elastically elongatable. The closure elements include a fastening material which is at least partially covered by a protective layer of nonwoven. The nonwoven here extends over the hooks of the fastening material with the result that fastening of the protective layer may be insufficient.

It is therefore an object of the invention to provide an absorbent article having at least one elastically elongatable panel, which can be produced in a cost-effective and simple manner and which permits reliable attachment of a fastening material.

It is believed that the object of the invention can be accomplished by joining at least one of the layers forming the elastically elongatable panel directly to the top surface of a fastening material in an area, which is free of any hook projections.

SUMMARY OF THE INVENTION

One aspect of the invention is directed to a closure element with elastic and non-elastic regions. The closure element comprises a nonwoven web, an elastically extensible film strip joined to the top surface of the nonwoven web, a nonwoven material disposed on top of the film strip and a strip of a fastening material disposed on top of the nonwoven web. The fastening material comprises a plurality of hook projections extending from a base and at least one region that is free of any hook projections. At least one of the elastically extensible film strip, and the nonwoven material overlaps with the region of the fastening material that is free of any hook projections.

Another aspect of the invention is directed to a closure element, which comprises a nonwoven web, an elastically stretchable film strip joined to the top surface of the nonwoven web, a nonwoven material disposed joined of the film strip, and a strip of a fastening material disposed on top of the nonwoven web. The fastening material comprises a plurality of hook projections extending from a top surface of a base and a plurality of projections extending from a bottom surface of the base. At least some of the protrusions extending from the bottom surface of the base penetrate the nonwoven web.

Another aspect of the invention is directed to an absorbent article, which comprises a liquid pervious layer, a liquid impervious layer and a core disposed between the liquid pervious layer and the liquid impervious layer. The absorbent article also includes at least one closure member.

BRIEF DESCRIPTION OF THE DRAWINGS

FIG. 3D is a schematic top view of a compound material web and closure members cut from the compound material web;

FIG. 4A is a schematic representation of a wider compound material of FIG. 3A;

FIG. 4B is a schematic representation of an elastically elongatable panel formed by cutting a portion of the compound material of FIG. 4A;

DETAILED DESCRIPTION OF THE INVENTION

Figure 1:
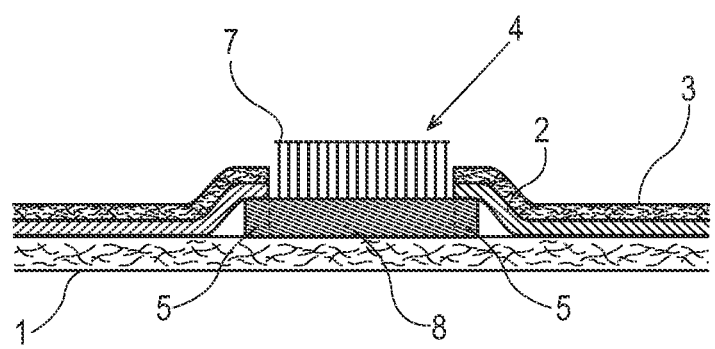
FIG. 1 is a schematic cross-section of a compound material web.

According to a first embodiment of the invention a compound material web comprises a least a strip of fastening material suitable for engaging a complementary fibrous web. The strip of fastening material comprises first and second longitudinal edges. The strip of fastening material comprises at least one region adjacent to one of the first and second longitudinal edges that is free of any hook projections and one region that includes hooks projections suitable for engagement of a fibrous web. As used herein, the terms "free of any hook projection," refers to a region of the strip of fastening material that is disposed along the length of the fastening material and has no hook projection. At least one of the regions that is free of any hook projections may overlap with two or more of the webs forming the compound material. As such, the strip of fastening material is more integral with the webs forming the compound material that are disposed inboard of the longitudinal side edges of the strip of fastening material. The compound web also comprises an elastic web, which can be formed by an elastically stretchable film strip. It can be advantageous for the elastic web to overlap with the strip of fastening material in particular in at least one of the regions that is free of any hooks. Without intending to be bound by theory, it is believed that even if the compound material web or the closure elements made from it are repeatedly stressed by application of a force in the cross direction of the closure element, the compound material web is less likely to tear in the vicinity of the fastening material because the strip of fastening material is more integral with the other webs forming the compound structure. One of ordinary skill will appreciate that in use, considerable forces are applied to the fastening material in particular at the interphase of the strip of fastening material and the webs forming the compound material web. It is also believed that contrary to already known closure elements that are suitable for absorbent articles and are known to require an additional and separate reinforcement material in order to prevent tearing of the closure element, a portion of the strip of fastening material, and more specifically the region that is free of any fastening material may be used instead to reinforce the compound material.

In one embodiment, the compound material web comprises a nonwoven material covering the film strips on a second side of the compound material web and includes spaced-apart nonwoven strips, such that the strip of fastening material is disposed transversely. The edges of the nonwoven strips may lie exactly along the edges of the elastically stretchable film strips that are disposed underneath the nonwoven strips. This can be achieved, for example, in that the elastically stretchable film strips and the nonwoven strips are provided in the form of portions of a corresponding pre-laminate. Starting from this common edge the elastically stretchable film strips as well as the nonwoven strips arranged on top of them may be of identical width or a different width. If the width of the nonwoven strip is different than the width of the elastically stretchable film strip, and in particular if the width of the nonwoven strip is greater than the width of the elastically stretchable film then there is area portion of the nonwoven strip that overlaps and is in direct contact with a flat nonwoven web. In this configuration, the elastically stretchable film is disposed between the individual nonwoven strips and the nonwoven web.

In one embodiment, the strips of nonwoven material may extend beyond the edges of the elastically stretchable film strips disposed underneath such that a portion of the nonwoven strip overlaps with a portion of the fastening material strip and in particular the region that is free of hook projections. This may be accomplished if the film strips and the nonwoven strips are supplied separately in the form of strips and then laminated simultaneously or directly one after the other, thereby making it unnecessary to provide a pre-laminate. With such a design it is possible, in particular, for the region(s) of the fastening material that is free of hook projections to be overlapped only by the strip of nonwoven material and not by the strips of elastically stretchable film. The edges of the elastically stretchable film strips are then disposed laterally outboard of the region that is free of hook projections thereby allowing a particularly even transition to be achieved, in particular if the thickness of the fastening material at its longitudinal edges is substantially equal to the thickness of the elastically stretchable film strips.

In one embodiment, a strip of fastening material is attached directly to the top surface of a nonwoven web. First and second elastically stretchable film strips are also attached to the top surface of the nonwoven web such that the first strip is disposed on one side of the strip of fastening material and the second strip of elastically stretchable film is disposed on an opposite side of the fastening material. A portion of each of the first and second strips elastically stretchable film may overlap and be joined to a longitudinal region of the fastening material that is free of hook projections.

One of ordinary skill will appreciate that there are several ways to join different materials to each other. For example, materials may be joined via an adhesive which is applied optionally across the entire surface or only in certain areas. Depending on the gluing method and the bonding technique strip-type gluing may be sufficient for safely attaching the strip of fastening material. Strip-type gluing offers additional savings since less adhesive is needed thus leading to a cost reduction. One of ordinary skill will appreciate that suitable adhesives are not only relatively expensive, but can also impair elasticity. This drawback can be mitigated by a strip-type application of the adhesive underneath the film strips. A strip-type application of adhesive in parallel with the extension of the elastically stretchable film strip is particularly advantageous.

The elastically stretchable film strip can be made of any suitable thermoplastic elastomer, wherein in particular a polymer chosen from at least one of styrene-butadiene-styrene block copolymers (SBS), styrene-isoprene-styrene block copolymers (SIS), styrene-ethene-butene-styrene block copolymers (SEBS), elastic polyethylene copolymers, elastic polypropylene copolymers, elastic polyurethane copolymers, elastic polyamide copolymers or a mixture of these polymers is suitable. Apart from using a mono layer film, coextruded films may also be used, such as for example coextruded films that include several identical layers. Films strips with a thickness between 10 and 130 µm are particularly suitable.

The strips of nonwoven material covering the top surface of the elastic strips and the nonwoven web disposed on the bottom surface of the elastic strips of the compound material web do not need to have elastomeric properties. But it is advantageous for each of the nonwoven materials (whether the strips of nonwoven web) to be stretchable or elongatable to a sufficient extent in order to form with the elastic strips the elastic areas of the compound material web. The necessary stretchability may, however, also be achieved by activating the compound material web through initial stretching during which the nonwoven layers are elongated to the point they may be partially destroyed, i.e. torn.

The nonwoven materials impart a soft feeling to the touch to the compound material web. Depending upon the construction of the compound material web the nonwoven materials, however, must also have a certain strength. This applies, in particular, to the above-described construction, in which the elastically stretchable film strips end laterally at the edges of the fastening material or abut against the edges of the fastening material without overlapping with a portion of the fastening material. The nonwoven material acts as the interphase between the elastically stretchable strips and the fastening material and prevents tearing in the area of the transition.

A method for producing a compound material web with elastic and non-elastic regions, from which closure elements for an absorbent article can be obtained, is described below. A fastening material is supplied in strip form, which comprises longitudinal region(s) that are free of any hook projections. The strip of fastening material is attached to the top surface of a nonwoven web. First and second elastically stretchable film strips and nonwoven strips are supplied and attached to the nonwoven web such that the film strips are disposed between the nonwoven web and the nonwoven strips and such that the longitudinal region(s) of the fastening material that are free of any hook projections are overlapped, at least partially, by the film strips and/or nonwoven strips.

The described method is suitable for producing the previously described compound material web by simple means. As already described with reference to the compound material web itself, the film strips may be connected, prior to connecting it with the nonwoven web, with a corresponding nonwoven strip to form a pre-laminate.

There are several possibilities available to join the individual elements of the compound material web. For example, the bottom surface of fastening material strip may be glued to the top surface of the nonwoven web in strip or line-form all over or alternatively section-wise only. By "glued all over," it is meant that the adhesive is applied all over the side bottom surface of the fastening material strip and/or the corresponding top surface of the nonwoven web. Due to the fibrous structure of the nonwoven web, pores or the like may remain, where therefore the glue doesn't stick.

When gluing is performed in sections, lines or strips of adhesive may be provided in longitudinal direction of the fastening material strip, which may be straight or may be form corrugations. Corrugated gluing has the advantage that the outer edges of the fastening material strip are also included in the gluing to a certain extent.

In the alternative, the various webs or strips may be mechanically bonded, ultrasonically bonded or thermo bonded.

It should be noted that in the event the elastic film strips together with the nonwoven strips are provided as portions of a corresponding pre-laminate, then during manufacture the strip of fastening material is preferably be attached to the nonwoven web in strip-form, and the portions of the pre-laminate must then be attached to the nonwoven web and to the fastening material in the overlapping area. Since the overlapping area between the strip pre-laminate and the strip of fastening material is relative small, particular attention should be paid to a reliable bond in this area. The different bonding methods described, i.e. full-face gluing or section-wise gluing or bonding by an ultrasound technique are feasible at all connecting points. Attaching the fastening material to the nonwoven web by means of ultrasound may however, prove difficult because many of the hook projections being destroyed by the local application of ultrasound. However, this drawback is mitigated if ultrasound bonding is applied only on the region of the fastening material strip that is free of any hook projections. In principle a combination of gluing and ultrasound bonding is also possible.

A further aspect of the invention relates to the forming of the strip of fastening material. This strip of fastening material is particularly suitable for the previously described compound material web, but can also be used in other areas. In order to form the strip of fastening material, a polymer melt is fed from a wide-slot-nozzle into a gap formed between a roll and a belt, which advances section-wise along the surface of the roll. The roll and/or the belt are structured in a way suitable for forming hook projections. Depending on the process used complete hooks may be formed with stems and heads at the end or only the stems of the hooks may initially be formed, and with the heads that are formed in a subsequent step.

Hook projections are understood to be elements which are suitable for engagement with an associated fibrous material, for example a knitted textile material or a nonwoven material with loops. The hook projections may comprise both bent-over ends on the stems and also mushroom-shaped caps as heads.

Since an initially liquid polymer melt is fed from the slot nozzle into the gap, the hook projections of the fastening material may be shaped in a variety of ways. For example the structure on portions of the belt or roll provided for forming the hook projections may be interrupted, so as to ensure that no hooks are formed in particular regions. In particular the structure may be interrupted in region (s) extending in the transverse direction and/or circumferential direction, thereby producing longitudinal region(s) that are free of any hook projections due to a planar surface.

Apart from producing regions which include hook projections and regions that are free of any hook projections, the roll nip and thus the local thickness of the fastening material produced by this method may be set by imparting a certain contouring to the belt and/or the roll. In particular the region(s) that is free of any hook projections, the thickness of the roll nip may be reduced due to a local increase of the thickness of the belt and/or the roll, so that in the areas structured for forming the hook projections, carrier or base portions are formed below the hooks, which compared to the region(s) that is free of any hook projections comprise an increased thickness. Such a step-like design is advantageous in particular if overlapping of materials is provided in the region(s) that is free of any hook projections as previously described. Contouring can also be produced or at least supported by a contoured extrusion-nozzle gap. Even if following extrusion the melt is still liquid or deformable, such a shaping by way of the contoured extrusion-nozzle gap will allow varying amounts of melt to be made available in some areas in order to make it easier when applying a certain contouring by way of the belt and/or the roll.

In a first embodiment the fastening material is formed by a smooth belt, also called a sleeve and a structured roll (chill roll), the stems of the hooks are produced by this structured roll, normally a cooled roll (chill roll).

As part of the structuring process indentations or cavities are formed in the roll for forming the stems of the hook projections. To this end the roll surface may undergo an etching procedure or be treated with a laser, for example. The number and distribution of the cavities may be adjusted to suit the respective application for which the fastening material strip to be formed is intended.

The belt may be produced entirely seamlessly by a galvanic process. Such a belt, which depending upon the application is also called a smoothing belt, is normally tensioned between two tempered rolls of which at least one roll is driven. The tensioned belt is normally pressed against the structured cooled roll by a retractable roll mill. Pressing the belt against the roll at a wrap angle, which is normally variably adjustable has the effect of the initially still liquid polymer melt filling the indentations or cavities of the structured roll. Additional venting is normally not necessary, not even for a multi-layer design of the roll. As the circulating belt is in contact with the roll while forming the stems of the hooks, cooling can be better controlled, thus permitting the use of very high production speeds during manufacture. By making use of the described belt it is also possible to produce an especially even, smooth and high-quality reverse side of the fastening material.

As previously discussed structuring may be interrupted in longitudinal, transverse or any random direction in order to produce one or more region(s) that is free of any hook projections.

In another embodiment, the strip of fastening material may be formed using a smooth roll and a structured or perforated belt. With a perforated belt sufficient venting of individual holes for producing the stems of the hooks is ensured in all circumstances. The thickness of the belt may be utilised to set the length of the stems to be formed. Alternatively the length of the stems may be set by means of the contact pressure with which the belt is pressed against the roll, wherein for a reduced contact pressure the holes of the perforation are only partially filled. By varying the contact pressure the height of the stems of the hooks may be varied without changing the belt.

Apart from an essentially point-shaped perforation or structuring of the roll or belt really larger projections may be provided on the belt or the roll in order to vary the gap between roll and belt in certain areas. Thus provision is made in a further variant for forming the strip of fastening material for the roll as well as the belt to be provided with a structuring and/or with projections. For example, the belt may be provided with perforations in certain sections, and the cooling roll is provided with projections which may for example extend linearly in circumferential direction or in transverse direction. Due to such a design the thickness distribution of the fastening material may be set. In particular it is possible that carrier or base portions formed below the hooks are of a greater thickness than the region(s) that is free of any hook projections. Advantageously, the reduced thickness of the material in the region(s) that is free of any hook projections provides the savings in material that can then be used to form the hook projections which protrude away from the base.

As discussed, there are several processes that can be used to manufacture the fastening material and form hook projections starting with a molten material having initially constant thickness. But it is observed that the flow or displacement of molten polymer into the individual holes to form the hook projections may result in a reduction of the base's thickness in the area under the hook projections. This reduction in thickness can be mitigated if not avoided by the flow of molten polymer coming from the side portion of the fastening material.

Due to structuring the roll and the belt it is also possible to form hook projections on both sides of the strip of fastening material.

If the belt is provided with perforations, the polymer melt can be initially pressed through the perforations and then bent over or pressed flat immediately by a further device for forming heads on the inboard side of the circulating belt. To this end for example, a further roll or an additional belt may be provided within the circulating belt.

Alternatively the head structure adjoining the stems may be produced in a subsequent process step, wherein the previously formed stems are thermally and/or mechanically deformed. Mechanical deforming of the stem ends for forming the heads takes preferably place in a roll nip in which at least one roll is driven and the roll facing the stem ends is heatable. In addition the hook ribbon may first be heated to a deforming temperature for which an infrared lamp is particularly suited. In addition the head structure may be formed by using an ultrasound technique, wherein the head structures are formed in the nip of a roll and a sonotrode due to a defined contact pressure using ultrasound.

With regard to the handling of the previously described compound material web, it may be advantageous to form the stems initially without heads or bent-over ends, and such that the shaping or head formation that is suitable for interlocking are not produced until after the entire compound material web is formed. It is believed that without any heads already formed, the compound material web can be wound and later unwound without any problems because the initially linear extending stems cannot get tangled up with the opposite fibrous material. The heads or bent-over ends are formed after the compound material web is unwound for further processing, i.e. in particular for manufacturing closure elements for absorbent articles.

As previously discussed the hook projections (i.e. stems and heads) or stems alone may alternatively be formed on both sides of the strip of fastening material. In particular, it is possible to form hooks on one side of the strip of fastening material and only stems on the other. If such a fastening material is used for manufacturing the previously described compound material web, the strip of fastening material with its linearly extending stems may be placed onto the continuous nonwoven web, which forms the first outer side of the compound material web. The stems then pierce this nonwoven web and protrude from it. The opposing hooks are then exposed as previously described on the opposite side and disposed between the strips of the nonwoven material provided on each. If several layers of such a compound material web are wound, the stems and hooks will lie on top of each other in subsequent layers, such that the underneath layer of the compound material web is kept at a distance due to the length of the stems, wherein also in the wound state the hooks are prevented from connecting individual layers in an undesirable manner.

Depending upon requirement and field of application the strip of fastening material may be of a single-layer or multi-layer construction and may consist of different materials. For a single-layer construction polyolefin-based materials are particularly suitable such as polyethylene (PE), polypropylene (PP), blends of the mentioned polymers as well as a copolymer of polyethylene and polypropylene. Especially preferred are stiff PP types which may be present as homopolymers or as copolymers. In addition other polymers are also suitable for a single-layer or multi-layer construction. Other advantageous and, by comparison, stiff materials are cycloolefin copolymer (COC), polystyrene (PS), polyesters such as polyethylene terephthalate (PET), polyamide (PA) such as PA 6 and PA 6.6 or polymethyl methacrylate (PMMA).

Due to a multi-layer construction of the hook ribbon conflicting requirements such as stiffness, flowability during manufacture and compatibility with adjacent layers in the laminate may be met in an advantageous manner. According to a first embodiment, substantially true-to-type constructions or at least constructions entirely of polyolefin are possible, which in particular promote recycling. In a three-layer construction for example, all layers may consist of polypropylene (PP), wherein however the layer from which the hooks are to be formed is selected to have a high melt flow rate (MFR), whereas the remaining layers are optimised to provide the desired stiffness of the hook ribbon.

Apart from such a true-to-type construction a multi-layer construction from different types of material is possible, such that polyolefin-based materials, in particular PP, are used in the outer layers. For a construction comprised of at least three layers one internal core layer may be chosen to provide the desired stiffness. In a five-layer construction, an adhesion-promoting layer is present between the core layer and the outer layers, the layers in a three-layer construction may be satisfactorily connected with each other by functionalised or modified polyolefins.

The thickness of the strip of fastening material at the region that is free of any hook projections and beneath the hooks is typically between 20 and 180 µm. If the regions that are free of any hook projections are not provided with a reduced thickness, the thickness at these regions as well as the thickness of the carrier portion arranged underneath the hooks is especially preferably between 70 and 140 µm. However, it should be noted that when the hook projections are formed, the carrier or base portion may be constricted to a certain degree in relation to the specified thickness.

With a one-layer construction of the strip of fastening material all portions of the fastening material are formed from the same polymer. With a multi-layer construction on the other hand, the hook projections are normally formed from the material of the respective outer layer. But if then the stiffness of the hooks is inadequate for a certain application, there is another possibility, whereby the hooks, for a multi-layer construction, are formed, at least partially from the material of an internal layer. With a multi-layer construction this may be achieved, for example, by reducing the thickness of the outer layer on which the hooks are produced to the point where the material of the layer underneath also becomes an essential part of the stems or hooks during a corresponding embossing operation.

The length of the hook projections is normally distinctly more than the thickness of a carrier or base portion of the fastening material on which the hooks are arranged. Preferably the length of the hooks is two to ten times, especially preferably three to seven times the thickness of the carrier portion below the hooks.

Finally the invention also relates to a fastening material in strip-form, in particular for the above-described compound material web, such that the fastening material comprises hook projections arranged on a carrier or base portion as well as one or more region(s) that is free of any hook projections. According to one embodiment the region that is free of any hook projections has a reduced thickness in relation to the carrier portion, such that the thickness of the region that is free of any hook projections is preferably less than 80% of the thickness of the carrier portion. The region that is free of any hook projections represents a surface that is preferably between 10% and 60% of the overall surface of the strip of fastening material. A fastening material of this kind offers the advantage that the region(s) that is free of any hook projections are comparatively thin making it easy for another material to be arranged there in an overlapping manner.

With reference to the above-described compound material web a particularly advantageous manufacture is possible. It will be appreciated that the fastening material below the hook projections must be of a sufficient thickness in order to hold the individual hooks. In the edge regions, however, the tensile forces are evenly distributed, meaning that here a lesser thickness is sufficient. As a result of reducing the thickness on the region that is free of any hook projections, individual hooks will initially project further in relation to the nonwoven material arranged on the second external side of the compound material web. It also makes the step smaller, which for the overlapping envisaged according to the invention must be bridged by the elastically stretchable film strips. As a result, the stability of the compound material web as a whole can thereby be improved.

The present invention will now be explained with reference to the drawings which merely show examples of embodiments.

FIG. 1 is a schematic representation of a compound material web that includes elastic and non-elastic portions, which can be used to make closure elements for absorbent articles. The compound material web comprises a first nonwoven web 1, which forms a first outer side of the compound material web. In order to produce the elastic sections of the compound material web, parallel and spaced-apart elastically stretchable materials 2 are disposed on the nonwoven web 1. The elastically stretchable or extensible materials 2 may be any suitable material which is capable of elongation when a force is applied thereto and is able to recover at least 10% of the elongation caused by the force when the force is released. It may be advantageous for the elastically stretchable materials 2 to be in the form of a film. In a preferred embodiment, each of the film strips 2 is covered by a separate nonwoven material 3 such that the film strips are at least partially disposed between the nonwoven web 1 and the nonwoven material 3. It can also be advantageous for the nonwoven material 3 to be in the form of nonwoven strips that covers the film strips 2 and in order to form a second outer side of the compound material web.

In addition a fastening material 4 is joined, preferably directly attached to the nonwoven web 1. In a preferred embodiment, the fastening material 4 is a mechanical type fastener and includes a base 8 and a plurality of hook projections 7 and is adapted to engagement with a complementary fibrous surface (not shown) as is well known in the art. In the embodiment shown in FIG. 1 the bottom surface of the 8 is attached directly to the top surface of the nonwoven web 1 and such that the region that is between the first and second elastically stretchable film strips 2 is bridged by the fastening material 4. It should be noted that the fastening material 4 is relatively stiff and non-stretchable thereby forming the non-elastic region of the compound material web. At least a portion of each of the elastic film strips 2 is joined to the fastening material 4 on respective sides of the fastening material 4 while portions of the nonwoven web 1, the elastic film strips 2 and the nonwoven material 3 remain elastically stretchable. The elastic properties of the compound material web are provided by the elastically stretchable film strips 2 and in particular the portions of the strip, which do not overlap with the base 8 of the fastening material 4. Prior to any first-time use by a consumer or end user, it may be advantageous to stretch the elastically elongatable region of the compound material web in its transverse direction, in order to "activate" the compound material web in the elastic regions, and such that is it more easily elongatable by a consumer or end user. It should be noted that even if activation is performed in this way, the non-elastic regions remain undisturbed because the fastening material 4 and in particular its base 8 is relatively stiff and non-extensible at the level of force that is sufficient to elongate the elastic regions.

In one embodiment, the fastening material 4 comprises at least one, but preferably two regions that are adjacent to regions 5 that are free of any hook projections and are adjacent to the longitudinal edges of the fastening material 4. At least one, but possibly both of these regions can be covered by a portion of the elastically stretchable film strips 2 respectively disposed on each side of the fastening material 4. In one embodiment, each of the regions that is free of any hook projections has a width of at least 15 mm, or at least 8 mm, or even at least 2 mm. Each of the regions that is free of any hook projections can have a width of less than 30 mm, or less than 20 mm, or even at least less than 10 mm. The film strips 2 can be attached in a suitable manner to the regions that are free of any hook projections 5 in order to minimize if not eliminate any weak region when a closure or fastening element is made from the compound material web and which may be subjected to a transverse force. Since the fastening material 4 is more integral with the other webs forming the compound material web because the film strips 2 overlap at least partially with the regions that are free of any hook projections 5, it is believed that no additional reinforcement is needed.

Figure 2:
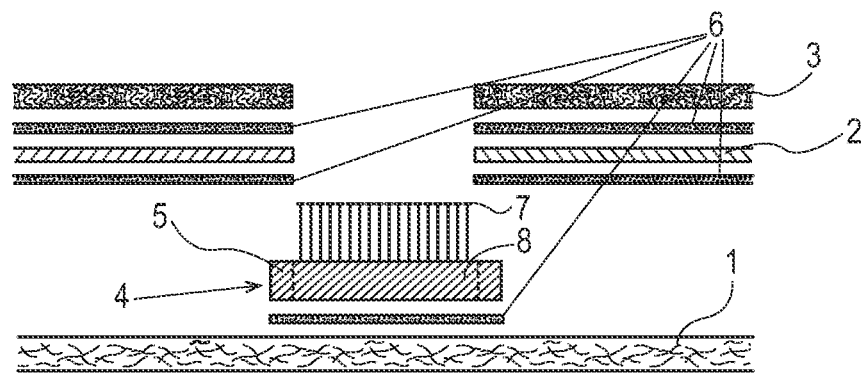
FIG. 2 is a schematic exploded view of FIG. 1.

In the embodiment shown in FIGS. 1 and 2 not only the film strips 2 but also the nonwoven material 3 and the fastening material 4 are supplied in the form of strips, which remain unchanged along the longitudinal direction. But one of ordinary skill will appreciate that the fastening material 4 can include one or more regions that are free of any hook projections such that these regions extend continuously or intermittently in the longitudinal direction or the transverse direction of the fastening material.

The attachment of the fastening material 4 to the nonwoven web 1 as well as the attachment of the elastically stretchable film strips 2 to the nonwoven web 1 and to the regions that are free of any hook projections 5 may be done in any suitable manner. In particular attachment may be done by what is known in the art as full-face gluing or section-wise or strip gluing via an adhesive 6 or via ultrasound-bonding. In the case of section-wise gluing, adhesive strips that extend along the longitudinal direction of the described strip-shaped elements are applied to at least one of the strip webs.

FIG. 2 is a schematic cross-section exploded view of the compound material web and shows its individual components, including a full-face application of adhesive 6, which is by way of example. Regarding the method for manufacturing a compound material web having elastic and non-elastics regions, a first step includes supplying a nonwoven web 1 and a fastening material 4, which has at least but preferably two regions that are free of any hook projections 5. The bottom surface of the fastening material 4 is then attached, for example by gluing with adhesive 6, to the top surface of the nonwoven web 1. In another step, the elastically stretchable film strips 2 and the nonwoven strips of the nonwoven material 3 are supplied and attached to the nonwoven web 1 such that that the film strips 2 are disposed between the nonwoven web 1 and the nonwoven material 3. In addition, at least a portion of the film strip and/or nonwoven strip 3 overlaps with at least a portion of, but preferably the whole region 5 of the fastening material that is free of any hook projections.

In another embodiment, the film strips 2 and the nonwoven material 3 may be bonded to each other to form a pre-laminate prior to being connected to the nonwoven web 1 and/or the fastening material 4.

Figure 3A:
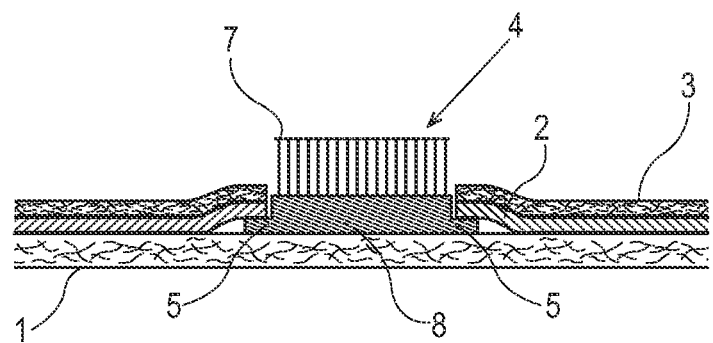
FIGS. 3A to 3C are alternative schematic cross-sectional representations of compound material webs suitable to make an elastically elongatable panel.
Figure 5A:
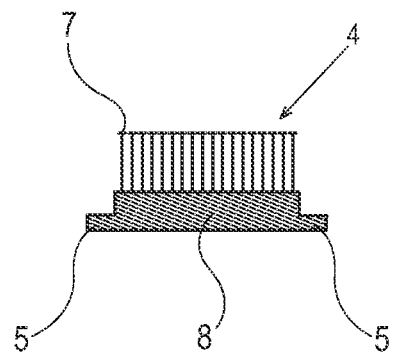
FIG. 5A is a schematic representation of a fastening material suitable for the invention.

FIG. 3A shows another embodiment of a compound material web that includes a fastening material 4 that is individually shown in greater detail in FIG. 5A. The fastening material 4 of this embodiment includes at least one, but preferably two regions 5 that are free of any hook projections and such that the thickness of the base 8 at region 5 is less than the thickness of the base 8 in the portion of the fastening material that includes the hook projections 7. It should be understood that the base 8 should be of a sufficient thickness in order to hold the hook projections 7 and in order to provide sufficient stiffness to the non-elastic region of the compound material web. It is also believed that regions 5 that are free of any hook projections and include a base with a reduced thickness provide significant material savings. It is also believed that various advantages are obtained with regard to the geometry. In addition, one of ordinary skill will understand that with such a reduced thickness, the film strips 2 and the nonwoven material 3 are less deformed in comparison to the embodiment shown in FIG. 1 (due to a smaller hump) resulting in an overall improvement in bond strength in the transverse direction of the compound material web. In addition, it is believed that when the nonwoven material 3 and/or the film strip 2 overlaps with a region 5 having a reduced thickness, more of the hook projections (i.e. a greater height) are available for engagement and penetrating a complimentary fibrous material.

Figure 3B:
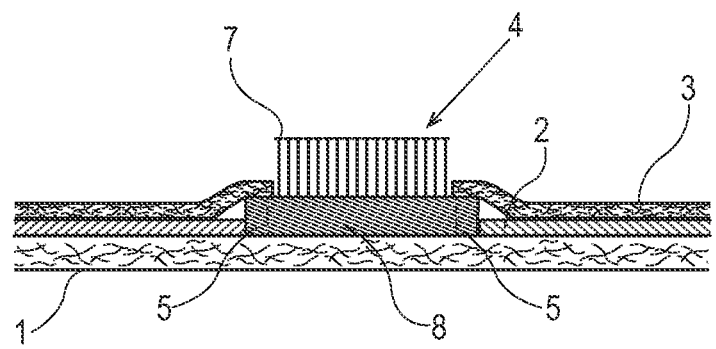
Figure 3C:
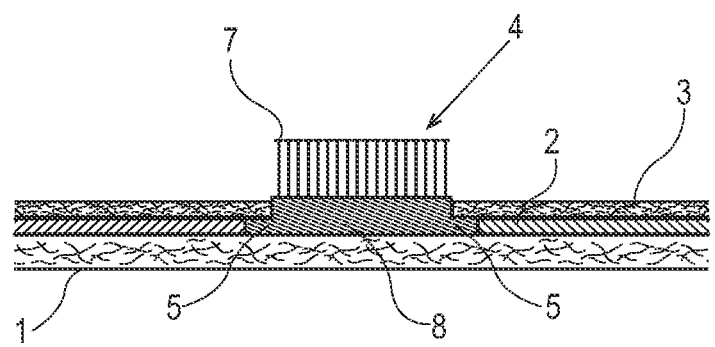

FIGS. 3B and 3C show alternative embodiments, where only one of the elastic film strip 2 and the nonwoven material 3 overlaps with the region 5 of the fastening material. It should be noted that in the embodiment shown in FIGS. 3B and 3C, the nonwoven material 3 overlaps with the region 5 of the fastening material whereas the elastic film strip does not overlap with the region 5. But in an alternative embodiment, an elastic film strip 2 overlaps with the region 5 of the fastening material whereas the nonwoven material 3 does not overlap with the region 5. In addition, FIGS. 1-3C show at least one of the elastic film strip and/or the nonwoven material 3 overlap by being disposed on top of base 8 at the region 5 of the fastening material. But an alternative embodiment where at least one of the elastic film strip 2, and the nonwoven material 3 overlaps with the region 5 by being disposed underneath the base 8 at the region 5 is also considered within the scope of the invention. It will be appreciated that when the elastic film strip does not overlap with the region 5 of the fastening material 5, the nonwoven web 1 and the nonwoven material 3 should be chosen to have sufficient tensile strength in the transverse direction in order to minimize if not eliminate the risk that a closure element may tear at the longitudinal side edge of the fastening material 4. It is also believed that when the base 8 at the region 5 has a reduced thickness, the resulting compound material web is "flatter" and substantially planar as shown in FIG. 3C in comparison to the compound material web of the embodiment shown in FIGS. 1, 3A and 3B. In particular, the thickness of the region 5 can be adapted to be substantially equal to the thickness of the elastically stretchable film strips 2 resulting in a rather small step/hump or no step at all on the nonwoven material 3.

As previously discussed, FIGS. 1 to 3C show schematic cross-sections of the compound material web from which individual closure elements suitable for absorbent articles can be cut or punched out. The compound material web may be cut within the fastening material 4, such that the cut fastening material 4 is disposed at one end of the closure element. The opposite end of the closure element can then be attached to an element of an absorbent article such as the chassis of an absorbent article, via an adhesive and/or mechanical bonding. A top view of a compound material web from which a plurality of closure members 20 are cut is schematically represented in FIG. 3D. In the embodiment shown in FIG. 3D, the closure elements are cut such that the distal end portion of the closure members include the base of the fastening material 4. The distal end portion may include a plurality of projection or be free of any hook projections while still including a portion of the base for added stiffness.

It is contemplated that the film strips 2 can have substantially the same width as the nonwoven material 3 thereon arranged in the form of nonwoven strips. It is, however, also possible for the nonwoven material 3 to be wider than the film strips 2 such that the nonwoven material 3 extends beyond the longitudinal side edge of the film strip 2. In particular, and as shown in FIG. 4A, two film strips 2 can joined to a single strip of the nonwoven material 3. A region of the nonwoven material 3 that is disposed between two consecutive film strips can then be joined directly to a region of the nonwoven web 1. Individual closure elements can then be cut along cut line 9 as shown in FIGS. 3D and 4A. One of ordinary skill will appreciate that the cut lines 9 are provided as an example and many alternative shapes are available to form a suitable closure element. For example, undulating or corrugated cutting or punching can be used resulting in increasingly narrower ends at the portion of the closure element that includes the fastening material.

Figure 5B:
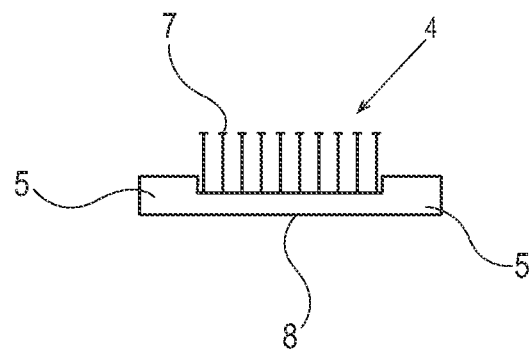
FIG. 5B is a schematic representation of another fastening material suitable for the invention.

There are several suitable methods to form a fastening material 4 with region or regions 5 that is/are free of any hook projections. In one embodiment, a fastening material that includes hook projections disposed all over its width (i.e. that are present substantially from one side edge to the opposite side edge) is provided. A plurality of the projections that are disposed in the vicinity of the side edges can then be cut close to the base in order to create one or more regions that is free of any hook projections. In another embodiment, the hook projections disposed in the vicinity of the side edges can be removed via the local application of heat and/or pressure. In addition, the thickness of the region(s) 5 can be reduced by compressing this region, which can provide the design shown in FIG. 5A. In another embodiment shown in FIG. 5B, the base 8 in the area below the hook projections can have a reduced thickness such that the tip or head of the hook projections is closer to the outer surface of the region 5 that is free of hook projections. Among other benefits, it is believed that such a fastening material is more flexible and feels softer to the touch while maintaining good engagement with a complementary receiving material. Although these methods are perfectly suitable to produce the region(s) 5, it is also believed that it may be advantageous to produce the region(s) 5 during the manufacture of the fastening material 4 instead of as a subsequent step.

Figure 6:
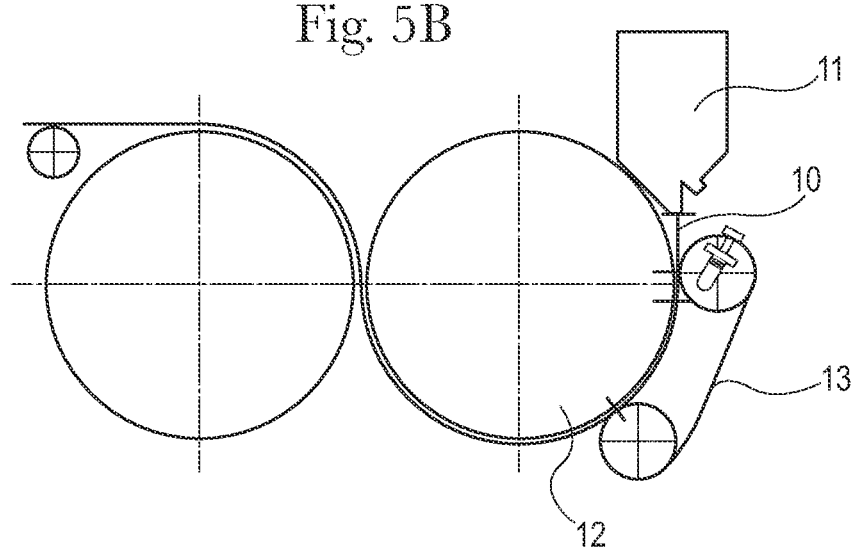
FIG. 6 is a schematic representation of a process suitable to make the fastening material of the invention.

In one embodiment represented in FIG. 6 a fastening material 4 can be formed by feeding a molten polymer 10 from a slot nozzle 11 into a gap present between a cooled roll 12 (also known as a chill roll) and a belt 13 that is capable of movement section-wise against the surface of roll 12. The roll 12 and/or the belt 13 comprise structuring such as hollow cavities, which are provided for forming the stems of hook projections 7. Such structuring can include indentations or cavities and may take the form of perforations in the case of the belt 13. The belt 13 which does not include structuring on its outer surface, is also called a smoothing belt or sleeve.

The structuring used to form the projections is substantially point-shaped in order to be able to form the stems of the hook projections. The region(s) 5 that is free of any hook projections can be formed during manufacture of the fastening material using the equipment and process shown in FIG. 6 when at least one of the roll 12 or the belt 13 have a corresponding portions having a smooth surface (i.e. portions without any structuring or a different structuring).

In addition to the fine surface structuring used to form individual hook projections 7, the roll and/or the smoothing belt may also include a particular surface topography, which can extend across a larger area of the outer surface of the roll and/or belt and which is suitable to impart a varying thickness to the base of the fastening material. By way of example, this varying thickness can be such that the thickness or gap at the roll nip has different values in certain sections. The varying surface topography can be obtained by including one or more protrusions or grooves on the outer surface of the roll and/or belt. The varying surface topography of the roll and/or belt can also be adapted to impart a reduced thickness to the base of the fastening material in particular in its region(s) 5 that is free of any hook projections.

Figure 7D:
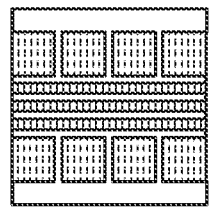
FIGS. 7A to 7D are schematic representations of alternative hook materials.
Figure 7H:
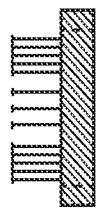
FIGS. 7E to 7H are schematic cross sectional representations of the hook materials shown in FIGS. 7A to 7D.

These methods are suitable to manufacture a fastening material in strip-form, which is particularly adapted for the above-described compound material web previously described. The fastening material may be used in many applications include the manufacture of closure elements. FIGS. 7A to 7D represent a schematic of a top view and corresponding schematic cross-section examples of different designs of the fastening material 4 that includes one or more regions 5 that is substantially of any hook projections. In FIG. 7A and corresponding FIG. 7E, a strip-shaped fastening material is shown which comprises first and second regions 5 that are disposed adjacent to the respective first and second longitudinal side edges of the strip. FIG. 7B and corresponding FIG. 7F, shows a fastening material with additional regions 5 that extend along the machine direction of the strip.

Figure 7C:
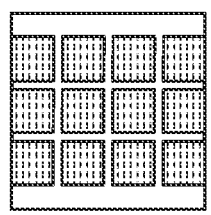
Figure 7G:
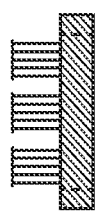
Figure 7B:
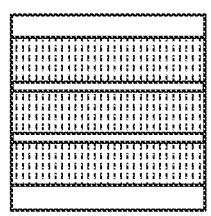
Figure 7F:
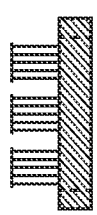
Figure 7A:
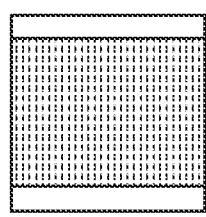
Figure 7E:
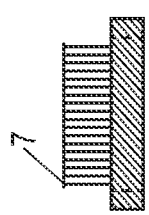
Figure 8A:
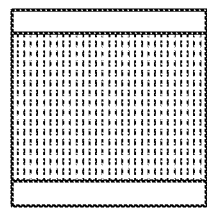
FIG. 8A to 8D are schematic representations of alternative hook materials that include a base layer having a varying thickness.
Figure 8B:
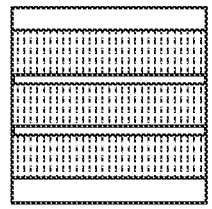
Figure 8C:
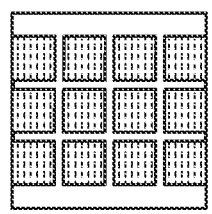
Figure 8D:
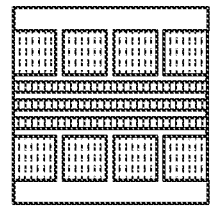
Figure 8E:
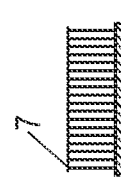
FIG. 8E to 8H are schematic cross-sectional representations of the hook materials of FIGS. 8A to 8D.
Figure 8F:
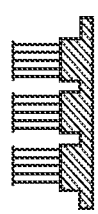
Figure 8G:
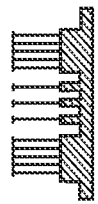
Figure 8H:
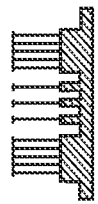

FIG. 7C, and corresponding FIG. 7G, shows additional regions 5 that are free of any hook projections and extend along the transverse direction of the strip. FIG. 7D, and corresponding FIG. 7H, shows a fastening material having a combination of regions 5 with some of the regions 5 extending along the machine direction of the strip and some of the regions 5 extending in the transverse direction of the strip. It can be advantageous for some of the regions 5 to be continuous without intersecting other regions 5. As explained above, in addition to the structuring for forming the hook projections 7, protrusions and grooves or recesses may be provided on the roll 12 and the belt 13 in order to vary the gap between roll 12 and belt 13.

With reference to the fastening material 4 the structuring for forming the hook projections 7 is a micro-structure, whereas the macroscopic structure of the fastening material 4 such as the varying thickness of its base is obtained via a combination of protrusions and recesses provided on the outer surface of the roll and/or belt. In particular the protrusions and recesses can be adapted to complement the structuring used to form the hook projections 7.

FIGS. 8A to 8D, and corresponding FIGS. 8E to 8H, show an alternative fastening material 4 having a similar arrangement or pattern hook projections and regions 5 that are free of any hook projections as the fastening materials shown in FIGS. 7A to 7D, which also include a base with a varying thickness. In particular, the thickness of the base 8 at the region(s) 5 is less than the thickness of the base at other portions of the fastening material.

Figure 9A:
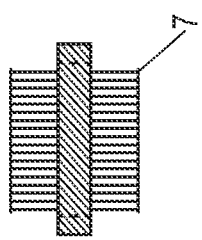
FIG. 9A to 9E are schematic representations of alternative hook materials that include hooks on both sides of the base layer.
Figure 9B:
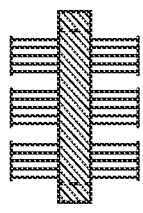
Figure 9C:
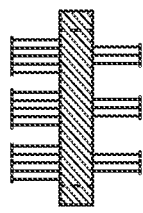
Figure 9D:
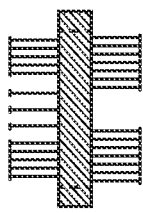
Figure 9E:
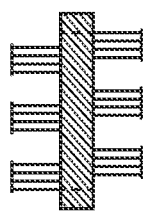

In another embodiment, each of the roll 12 and the belt 13 can include structuring in order to form hook projections 7 such that a fastening material 4 with hook projections 7 extending for both the bottom and the top surface of the base 8 can be produced. FIGS. 9A through 9D show a fastening material similar to the fastening material of corresponding FIGS. 7A to 7D in that the they have the same pattern of hook projections extending from the top surface of the base. The fastening materials shown in FIGS. 9A to 9D also include hook projections 7 extending from the bottom surface of the base 8. The pattern of hook projections may be the same of the top and bottom surface of the base a shown in FIG. 9A or 9B. But the pattern of hook projections extending from the top surface of the base may be different from the pattern of hook projections extending from the bottom surface of the base as shown in FIGS. 9C to 9E. The hook projections extending from the top surface of the base may also have a different length than at least some of the hook projections extending from the bottom surface of the base. FIG. 9E shows a fastening material having hook projections extending from the top surface of the base and hook projections extending from the bottom surface of the base and such that at least some of the hook projections present on the top surface do not overlap with some of the hook projections present on the bottom surface. It can also be preferred that none of the hook projections present on the top surface overlap with any of the hook projections present on the bottom surface of the base.

The fastening material 4 can be made of any polymeric resin known in the art but is preferably made of polyolefin, such as polyethylene, polypropylene, copolymers from PE and PP or mixtures of any of these compositions. The fastening material may be formed one of a single layer, but a multi-layer construction, in particular a five-layer construction, is also within the scope of the invention. With a multi-layer construction there is also the possibility of including an internal layer or, if the hooks 7 are arranged on one side only of the fastening material 4, of forming an outside layer opposite the hooks 7 with increased strength in order to make the material as strong as possible. In particular, if such a layer extends in the region 5, good strength can nevertheless be achieved, even at fairly small thicknesses.

Figure 10:
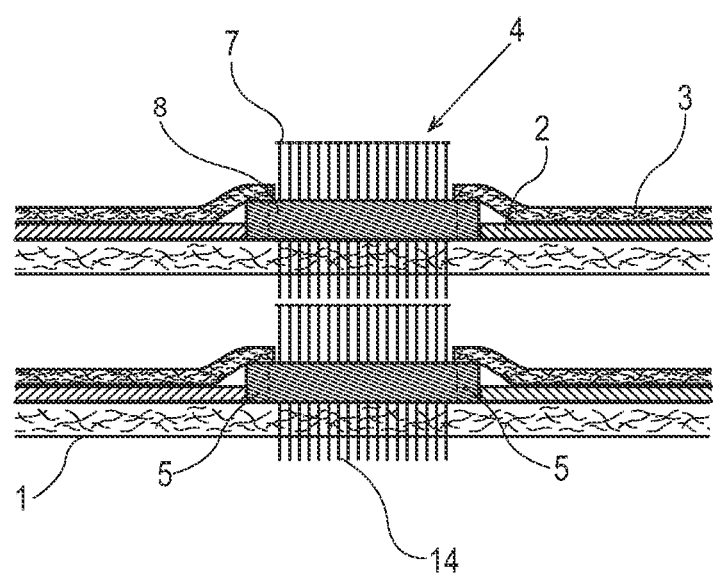
FIG. 10 is a schematic cross-sectional representation of a compound material web having hook projections extending from both top and bottom surface of the base.

FIG. 10 shows a practical example of a possible application and benefits of having hook projections extending from both top and bottom surface of the base. The fastening material shown in FIG. 10 includes fully formed hook projections (for example with stems and head or caps) extending from the top surface of the base and partially formed hook projections 14 (for example projections which only include stems and no head or cap) extending from the bottom surface of the base.

The hook projections on the top surface are arranged as previously discussed and shown in the context of FIG. 1 and the stems 14 are disposed against and penetrate through and extending past the nonwoven web 1. Among other benefits, the stems 14 provide good mechanical engagement between the fastening material 4 and the nonwoven web 1. In addition, and by extending past the nonwoven web 1, the stems 14 act as spacers when the compound material web is wound to form a roll of several layers and can prevent the fully formed hook projections 7 from engaging the adjacent nonwoven web 1.

During further processing and after unwinding of the compound material web, the stems 14 can then be trimmed or fused with the nonwoven web 1 using pressure and/or heat thereby providing additional stiffness to the fastening material.

Figure 11:
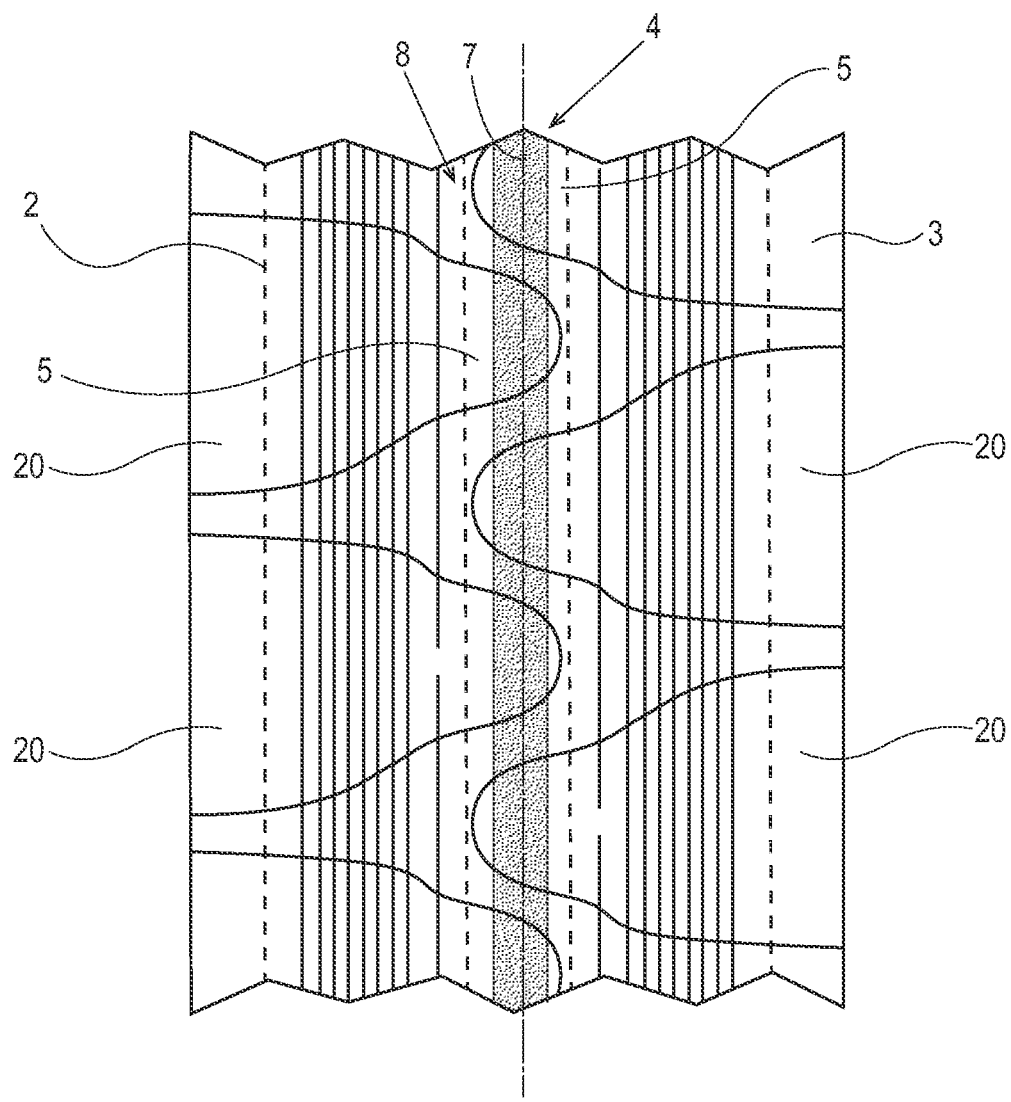
FIG. 11 is a schematic top view of a compound material web with the contour of several closure elements.

As previously discussed, the compound material web can be cut to form closure elements that are suitable for articles such as disposable or reusable absorbent articles. As shown in FIG. 4A and more particularly 4B, the compound material web can be cut such that the distal end or edge of the closure member is disposed within and overlaps with the portion of the fastening material 4 that includes a plurality of hook projections. In another embodiment, a closure member can be cut from the compound material web such that at least a portion of its distal end is disposed outboard and does not overlap with the portion of the fastening material 4 that includes a plurality of hook projections. As previously discussed, it can also be advantageous for the closure element to include a proximal portion that is such that the nonwoven web 1 is joined and in direct contact with the nonwoven material 3. FIG. 11 is a schematic top view of a compound material web and the contour of a plurality of closure members 20. In the embodiment shown in FIG. 11, and contrary to the embodiment represented in FIG. 3D, at least a portion of the distal end of the closure members include substantially no hook projections and form a finger tab that can be lifted and pulled by a user or a consumer. It can be advantageous for improved strength of the finger tab to have this portion of the distal end overlap with a portion of a region 5 of the fastening material 4, which includes substantially no hook projection. As a result, this portion of the distal end can also include and overlap with a portion of the film strip 2 and/or the nonwoven material 3. Closure elements can be shaped such that these can be nested as shown in FIG. 11 in order to minimize material waste. By leaving a gap between each of the closure elements, it is also possible to remove a single piece of trim by winding this piece after the closure elements are cut. The particular closure elements shown in FIG. 11 are asymmetric relative to the transverse axis of the closure element. The compound material web is preferably activated before the individual closure elements are cut. One suitable method to activate the web is to use a pair of intermeshing rolls also known as ring-rolls.

Figure 12:
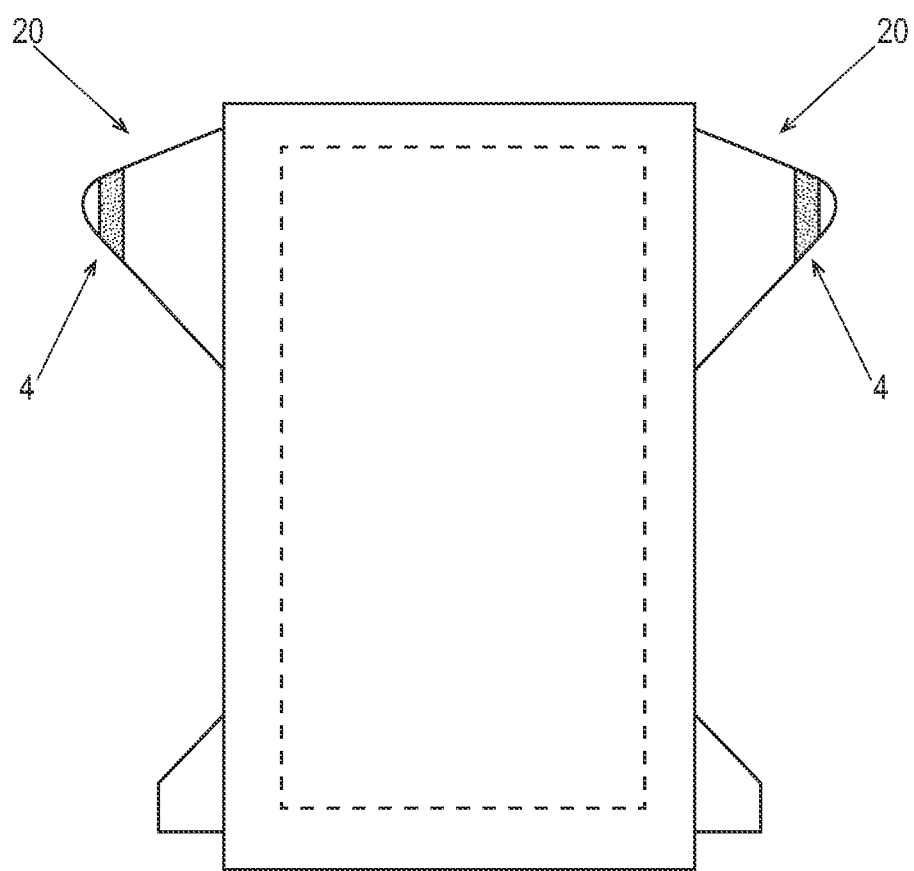
FIG. 12 is a schematic top view of an absorbent article that includes a pair of closure elements.

As previously discussed, closure members made from any of the previously discussed compound material webs are suitable for use with absorbent articles such as for example infant or adult diapers. In an embodiment shown in FIG. 12, at least one but preferably a pair of closure elements 20 are attached to the chassis of an absorbent article. The chassis may include a liquid pervious layer (also known as a topsheet), a liquid impervious layer (also known as a backsheet) and a core disposed between the liquid pervious layer and the liquid impervious layer. The core is adapted to absorb and retain liquids, such as for example urine. In one embodiment, a pair of closure members is disposed in an end section of the chassis, which in the case of an infant diaper can be the back waist section of the chassis. A non-limiting example of an absorbent article that includes a pair of closure elements is represented in FIG. 12.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A closure element with elastic and non-elastic regions comprising:
   a nonwoven web;
   an elastically extensible film strip joined to the top surface of the nonwoven web;
   a nonwoven material disposed on top of the film strip; and
   a strip of a fastening material disposed on top of the nonwoven web, wherein the fastening material comprises a plurality of hook projections extending from a base, and at least one region that is free of any hook projections, wherein at least one of the film strip and the nonwoven material overlaps with the region that is free of any hook projections such that the at least one of the film strip and the nonwoven material is disposed on top of the region that is free of any hook projections.

2. The closure element of claim 1 wherein the fastening material comprises a second region that is free of any hook projections, wherein the first region is adjacent to a first side edge of the fastening material and the second region is adjacent to a second side edge of the fastening material.

3. The closure element of claim 2 wherein at least one of a second elastically extensible film strip and a second nonwoven material overlaps with the second region that is free of any hook projections.

4. The closure element of claim 1 wherein each of the film strip and the nonwoven material overlap the region that is free of any hook projections of the fastening material.

5. The closure element of claim 1 wherein the base of the fastening material has a varying thickness such that the thickness of the base at the region that is free of any hook projections is less than the thickness of the base at the region which includes a plurality of hook projections.

6. The closure element of claim 1 wherein the nonwoven web is wider than at least one of the film strip and the nonwoven material.

7. The closure element of claim 6 wherein each of the nonwoven web and the nonwoven material is wider than the film strip such that at least a portion of the nonwoven web is joined and is in direct contact with the nonwoven material.

8. A closure element comprising:
   a nonwoven web;
   an elastically stretchable film strip joined to the top surface of the nonwoven web;
   a nonwoven material disposed on the film strip; and
   a strip of a fastening material disposed on top of the nonwoven web, wherein the fastening material comprises a plurality of hook projections extending from a top surface of a base, and a plurality of projections extending from a bottom surface of the base, wherein at least some of the projections extending from the bottom surface of the base penetrate the nonwoven web.

9. The closure element of claim 8 wherein at least some of the projections extending from the bottom surface of the base extend beyond the nonwoven web.

10. The closure element of claim 8 wherein the projections extending from the bottom surface of the base include a stem and do not include a head adapted to engage fibers.

11. The closure element of claim 8 wherein the hook projections extending from the top surface of the base have a height and the projections extending from the bottom surface of the base have a height, wherein the height of the hook projections is different than the height of the projections.

12. The closure element of claim 8 wherein the hook projections extending from the top surface of the base form a first pattern and the projections extending from the bottom surface of the base form a second pattern, wherein the first pattern is different than the second pattern.

13. An absorbent article comprising:
   a liquid pervious layer;
   a liquid impervious layer;
   a core disposed between the liquid pervious and the liquid impervious layers; and
   a closure element wherein the closure element comprises:
      a nonwoven web;
      an elastically extensible film strip joined to the top surface of the nonwoven web;
      a nonwoven material bonded on top of the film strip; and
      a strip of a fastening material disposed on top of the nonwoven web, wherein the fastening material comprises a plurality of hook projections extending from a base and at least one region that is free of any hook projections and wherein at least one of the film strip and the nonwoven material overlaps with the region of the fastening material that is free of any hook projections such that the at least one of the film strip and the nonwoven material is bonded to a top surface of the region that is free of any hook projections.

14. The absorbent article of claim 13 wherein the fastening material comprises a second region that is free of any hook projections, wherein the first region is adjacent to a first side edge of the fastening material and the second region is adjacent to a second side edge of the fastening material.

15. The absorbent article of claim 14 wherein at least one of a second elastically extensible film strip and a second nonwoven material overlaps with the second region that is free of any hook projections of the fastening material.

16. The absorbent article of claim 13 wherein each of the film strip and the nonwoven material overlap the region that is free of any hook projections.

17. The absorbent article of claim 13 wherein the base of the fastening material has a varying thickness such that the thickness of the base at the region that is free of any hook projections is less than the thickness of the base at the region which includes a plurality of hook projections.

18. The absorbent article of claim 13 wherein the nonwoven web is wider than at least one of the film strip and the nonwoven material.

19. The absorbent article of claim 18 wherein each of the nonwoven web and the nonwoven material is wider than the film strip such that at least a portion of the nonwoven web is joined and is in direct contact with the nonwoven material.

20. The absorbent article of claim 13 wherein the hook projections extend from a top surface of a base and the fastening material comprises a plurality of projections extending from a bottom surface of the base, wherein at least some of the projections extending from the bottom surface of the base penetrate the nonwoven web.

\* \* \* \* \*